US012127873B2

(12) United States Patent
DeFreitas et al.

(10) Patent No.: US 12,127,873 B2
(45) Date of Patent: Oct. 29, 2024

(54) HEATING SYSTEMS AND METHODS FOR HEATING A BREAST SUPPORT PLATFORM PRELIMINARY CLASS

(71) Applicant: Hologic, Inc., Marlborough, MA (US)

(72) Inventors: Kenneth F. DeFreitas, Patterson, NY (US); Tarpit Patel, Farmington, CT (US); Alan Rego, Woodbury, CT (US); Danielle Niremberg, New York, NY (US); Douglas Myers, Danbury, CT (US); Shusheng He, Newark, DE (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 18/366,760

(22) Filed: Aug. 8, 2023

(65) Prior Publication Data

US 2024/0108296 A1    Apr. 4, 2024

Related U.S. Application Data

(63) Continuation of application No. 17/314,806, filed on May 7, 2021, now Pat. No. 11,759,153, which is a
(Continued)

(51) Int. Cl.
*A61B 6/04*  (2006.01)
*A61B 6/50*  (2024.01)
*A61B 6/02*  (2006.01)

(52) U.S. Cl.
CPC ............ *A61B 6/502* (2013.01); *A61B 6/0414* (2013.01); *A61B 6/045* (2013.01); *A61B 6/025* (2013.01); *A61B 2562/0271* (2013.01)

(58) Field of Classification Search
None
See application file for complete search history.

(56) References Cited

U.S. PATENT DOCUMENTS 2,859,322 A    11/1958  Glazier et al.
3,900,654 A     8/1975  Stinger
(Continued)

FOREIGN PATENT DOCUMENTS

CN    102636950 A    8/2012
CN    206880685 U    1/2018
(Continued)

OTHER PUBLICATIONS

PCT Invitation to Pay Additional Fees and Partial Search Report in PCT Application PCT/US2019/052251, mailed Dec. 12, 2019, 15 pages.
(Continued)

*Primary Examiner* — Thomas R Artman
(74) *Attorney, Agent, or Firm* — Merchant & Gould P.C.

(57) ABSTRACT

A breast support platform for an x-ray imaging system includes a housing having a compression plate and a front wall, and a heating system disposed at least partially within the housing. The heating system is configured to heat at least a portion of the compression plate, at least a portion of the front wall, or at least a portion of the compression plate and the front wall. In an example, the heating system includes a transparent conducting film coupled to an inner surface of the housing. In another example, the heating system includes a blower disposed at least partially within the housing, and the blower is configured to channel hot air across an inner surface of the housing.

19 Claims, 13 Drawing Sheets

Related U.S. Application Data continuation of application No. 16/577,428, filed on Sep. 20, 2019, now Pat. No. 11,033,242.

(60) Provisional application No. 62/734,748, filed on Sep. 21, 2018.

(56) References Cited

U.S. PATENT DOCUMENTS

| | | | |
|---|---|---|---|
| 4,943,986 A * | 7/1990 | Barbarisi | A61B 6/502 |
| | | | 378/208 |
| 5,081,657 A | 1/1992 | Klawitter | |
| 6,803,543 B2 * | 10/2004 | Argersinger | A61F 7/007 |
| | | | 219/217 |
| 7,142,631 B2 | 11/2006 | Galkin | |
| 7,251,309 B2 | 7/2007 | Galkin | |
| 7,508,905 B2 | 3/2009 | Bohrisch | |
| 7,624,387 B2 * | 11/2009 | Yoshida | G06F 8/4441 |
| | | | 717/151 |
| 7,729,470 B2 * | 6/2010 | Fischer | A61B 6/045 |
| | | | 378/208 |
| 7,876,876 B2 | 1/2011 | Ohta | |
| 8,089,030 B2 | 1/2012 | Harrington | |
| 8,861,686 B2 * | 10/2014 | Kim | G21K 1/062 |
| | | | 378/154 |
| 9,610,051 B2 | 4/2017 | Beekman | |
| 9,743,895 B2 * | 8/2017 | Ko | A61B 6/4488 |
| 10,085,704 B2 | 10/2018 | Kim | |
| 11,033,242 B2 | 6/2021 | DeFreitas | |
| 11,759,153 B2 | 9/2023 | DeFreitas | |
| 2003/0121899 A1 | 7/2003 | Argersinger | |
| 2004/0056020 A1 | 3/2004 | Helmreich et al. | |
| 2004/0205738 A1 | 10/2004 | Yoshida et al. | |
| 2004/0206738 A1 | 10/2004 | Argersinger | |
| 2005/0287891 A1 | 12/2005 | Park | |
| 2006/0050844 A1 | 3/2006 | Galkin | |
| 2007/0019785 A1 | 1/2007 | Galkin | |
| 2008/0107232 A1 | 5/2008 | Bohrisch | |
| 2008/0247508 A1 | 10/2008 | Harrington | |
| 2008/0253512 A1 * | 10/2008 | Fischer | A61B 6/502 |
| | | | 378/209 |
| 2009/0080606 A1 | 3/2009 | Ohta | |
| 2012/0201353 A1 * | 8/2012 | Kim | G21K 1/062 |
| | | | 378/143 |
| 2014/0294142 A1 | 10/2014 | Choi | |
| 2014/0341336 A1 | 11/2014 | Kim | |
| 2015/0164449 A1 | 6/2015 | Ko | |
| 2017/0020467 A1 | 1/2017 | Beekman | |
| 2017/0340303 A1 * | 11/2017 | Stango | A61B 90/17 |
| 2018/0161198 A1 | 6/2018 | Gaiser | |
| 2020/0093445 A1 | 3/2020 | DeFreitas | |
| 2021/0259646 A1 | 8/2021 | DeFreitas | |
| 2024/0108296 A1 * | 4/2024 | DeFreitas | A61B 6/502 |

FOREIGN PATENT DOCUMENTS

| | | |
|---|---|---|
| DE | 102006038066 | 2/2008 |
| JP | 2003-157957 | 5/2003 |
| JP | 2005-349207 | 12/2005 |
| JP | 2008-534992 | 8/2008 |
| JP | 2009-082230 | 4/2009 |
| JP | 2010-035622 | 2/2010 |
| JP | 2015-054132 | 3/2015 |
| JP | 2019047999 | 3/2019 |
| KR | 20140118423 | 10/2014 |
| KR | 20190136546 | 12/2019 |
| WO | 2006096401 | 9/2006 |
| WO | 2014157792 | 10/2014 |
| WO | 2017/129663 | 8/2017 |
| WO | 2020/069348 | 4/2020 |

OTHER PUBLICATIONS

PCT International Search Report and Written Opinion in International Application PCT/US2019/052251, mailed Feb. 4, 2020, 16 pages.

PCT International Search Report and Written Opinion in International Application PCT/US2019/053507, mailed Dec. 16, 2019, 12 pages.

PCT International Preliminary Report on Patentability in International Application PCT/US2019/052251, mailed Apr. 1, 2021, 11 pages.

* cited by examiner

HEATING SYSTEMS AND METHODS FOR HEATING A BREAST SUPPORT PLATFORM PRELIMINARY CLASS

CROSS-REFERENCE TO RELATED APPLICATIONS

This application is a continuation of U.S. patent application Ser. No. 17/314,806, now U.S. Pat. No. 11,759,153, filed May 7, 2021, which is a continuation of U.S. patent application Ser. No. 16/577,428, now U.S. Pat. No. 11,033,242, filed Sep. 20, 2019, which claims priority to U.S. Provisional Application No. 62/734,748, filed Sep. 21, 2018, which are hereby incorporated by reference herein in their entireties.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed in an imaging area on a breast support platform that typically is flat, and the paddle then compresses the breast, usually while a technologist or other health professional is holding the breast in place. The technologist may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Some known discomfort may occur from the temperature of the breast compression system. Generally, the imaging systems are disposed within a relatively cold room for imaging system performance. As such, during breast compression, the compression system, including, the support platform and the paddle, are often perceived by the patient as cold, especially to the sensitive skin of a breast.

SUMMARY

In one aspect, the technology relates to a breast support platform for an x-ray imaging system, the support platform including: a housing including a compression plate and a front wall; and a heating system disposed at least partially within the housing and configured to heat at least a portion of the compression plate, at least a portion of the front wall, or at least a portion of the compression plate and the front wall.

In an example, the heating system includes a transparent conducting film coupled to an inner surface of the housing. In another example, the transparent conducting film includes a resistivity of between 14 and 24 ohm/square. In still another example, the heating system further includes a power source configured to produce approximately 24 volts at approximately 50 watts. In yet another example, a transfer adhesive secures the transparent conducting film to the inner surface. In an example, the transfer adhesive is substantially devoid of dust and/or air bubbles.

In another example, an imaging area is defined on the compression plate, and the heating system further includes one or more electrical contact points disposed on the transparent conducting film and outside of the imaging area. In still another example, the housing further includes two sidewalls substantially orthogonal to both the compression plate and the front wall, and the one or more electrical contact points are disposed proximate the sidewalls. In yet another example, the transparent conducting film is positioned between the inner surface of the housing and the one or more electrical contact points. In an example, the one or more electrical contact points are at least partially encapsulated by the transparent conducting film. In another example, the inner surface is proximate to at least a portion of the compression plate, at least a portion of the front wall, or at least a portion of the compression plate and the front wall.

In still another example, a recess is defined at least partially within the inner surface of the front wall, and the transparent conducting film is disposed at least partially within the recess. In yet another example, the transparent conducting film is adjacent to at least a portion of the compression plate and the front wall. In an example, the transparent conducting film is configured to heat the compression plate independently from the front wall. In another example, the heating system includes a conductor element embedded within the housing. In still another example, the conductor element is a carbon fiber based material.

In yet another example, the heating system further includes one or more electrical contact point in direct electrical contact with the conductor element. In an example, the compression plate includes the conductor element. In another example, the heating system includes a blower disposed at least partially within the housing, and the blower is configured to channel hot air across an inner surface of the housing. In still another example, the heat system further includes a heating element proximate the blower. In yet another example, the heat system further includes a baffle proximate the blower.

In an example, the heating system further includes a temperature sensor, and the heat generated by the heating system is at least partially based on the temperature measured by the temperature sensor. In another example, the temperature sensor includes one or more thermocouples. In still another example, the temperature sensor is disposed proximate the compression plate and opposite of the front wall. In yet another example, the heating system is entirely enclosed within the housing.

In another aspect, the technology relates to a method of heating a breast support platform of an x-ray imaging system, the method including: generating heat through a heating system disposed at least partially within a housing of the breast support platform, wherein the housing includes a compression plate and a front wall; and channeling the heat generated towards at least a portion of the compression plate, at least a portion of the front wall, or at least a portion of the compression plate and the front wall.

In an example, generating heat includes inducing an electric current flow across a transparent conducting film coupled to an inner surface of the housing. In another example, the transparent conducting film is adjacent to at least a portion of the compression plate and the front wall, and inducing the electric current flow includes independently controlling the current applied to the transparent conducting film at the compression plate and the current applied to the transparent conducting film at the front wall. In still another example, generating heat includes inducing an electric current flow directly across the compression plate. In yet another example, generating heat includes heating a flow of air and blowing the hot air across an inner surface of the housing. In an example, the method further includes measuring a temperature of the support platform. In another example, the heat generated by the heating system is at least partially based on the temperature measured by the temperature sensor.

In another aspect, the technology relates to a compression system for an x-ray imaging system, the compression system including: a support arm; a breast support platform coupled to the support arm and including a compression surface and a rear portion; and a heating system disposed at least partially within the support arm and configured channel a flow of air across the compression surface, wherein the heating system includes an outlet that is proximate the rear portion and oriented in a substantially downwards direction relative to the compression surface.

In an example, the rear portion extends upward from the compression surface and includes a curved section. In another example, the support arm includes at least one inlet.

In another aspect, the technology relates to a compression paddle for an x-ray imaging system, the compression paddle including: a compression plate; a front wall; and a heating system configured to heat at least a portion of the compression plate, at least a portion of the front wall, or at least a portion of the compression plate and the front wall.

In an example, the heating system includes a transparent conducting film. In another example, a transfer adhesive secures the transparent conducting film to the compression plate. In still another example, the one or more electrical contact points are at least partially encapsulated by the transparent conducting film.

In another aspect, the technology relates to a method of immobilizing a patient's breast on an x-ray imaging system, the method including: heating at least a portion of a compression surface of one of a support platform and a compression paddle to a first temperature, wherein a compression surface of the other one of the support platform and the compression paddle is at a second temperature; positioning the patient's breast on the compression surface of the support platform; and moving the compression surface of the compression paddle towards the support platform so as to compress the patient's breast between the two compression surfaces.

In an example, the method further includes heating at least a portion of the compression surface of the other one of the support platform and the compression paddle to the second temperature. In another example, the first temperature is different than the second temperature. In still another example, the temperature difference is at least 5° C. In yet another example, the method further includes imaging the compressed breast in at least one of a mammography mode, a tomosynthesis mode, and a CT mode.

DETAILED DESCRIPTION

Figure 1A:
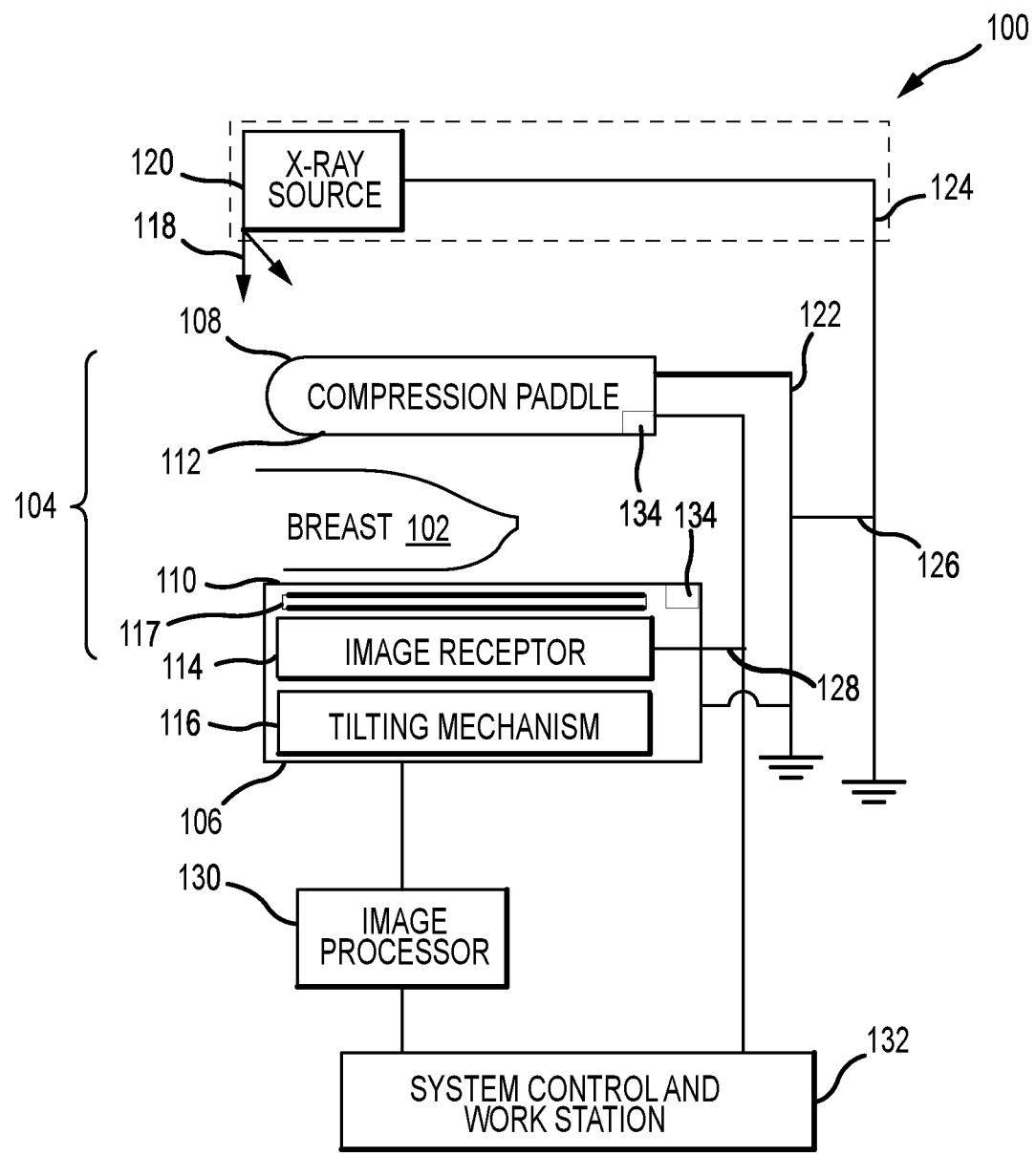
FIG. 1A is a schematic view of an exemplary imaging system.

The technologies described herein relate to a breast compression and imaging system that utilizes a heating system disposed at least partially within the support platform and/or compression platform of a compression system. The heating system is configured to heat at least a portion of a compression surface so as to reduce patient discomfort and anxiety during the breast compression and imaging process. By heating at least a portion of the compression surface, the patient may be less sensitive to the touch of the compression system (as it may be closer to room or body temperature), and thus, reduce undesirable movement of the patient and increase the efficiency of the technologist positioning and adjusting the patient's breast as well as experiential comfort for the patient.

In some known heating systems, the heating system is disposed externally from the support platform and channels (e.g., blows) hot air across the compression surface and directly on the patient's breast. These systems, however, can be loud and difficult to properly position on an imaging system. As to the latter aspect, the channel openings may allow for accidental infiltration of bodily fluids (e.g., sweat or blood—if biopsies are performed with the system). Further, such blown-air heating systems may require space otherwise needed for other system components (e.g., a biopsy device). In other known heating systems, a heating pad may be positioned on top of the support platform, but these need to be removed before patient use. In still other known heating systems, the heating element may undesirably interfere the x-ray receptor because of the heat and/or electromagnetics. In contrast, the heating systems described herein, are disposed within the support platform and/or at least partially embedded within a compression plate so that they can be used during the compression and imaging procedures and do not require penetration or openings proximate the breast. Additionally, the heating systems require less space than prior systems. To enable these features, the heating systems described herein are disposed within the support platform and are constructed so as to not form undesirable image artifacts. They heating systems are further positioned so as to not impede the function of the other components within the support platform (e.g., an image receptor and/or an anti-scatter grid).

In one aspect, the heating system can include a transparent conducting film that is adhered to the non-patient contacting side of the compression surface. The transparent conducting film receives a flow of electric current such that heat is generated, which then conducts through the housing and towards the compression surface. Through use of the transparent conducting film, the compression surfaces may receive heat from a heat source for patient comfort. Furthermore, the transparent conducting film is radiolucent so that image artifacts are reduced or eliminated in the x-ray images. Additionally, the transparent conducing film is relatively thin so that it can fit between the support platform housing and the image receptor, and does not undesirably affect the profile of the support platform housing. The thin low profile of the transparent conducing film also reduces or eliminate interferences with the x-ray receptor (e.g., via temperature and/or electromagnetics). In other examples, the heating system can be at least partially embedded within the housing so that the resistive heating element (e.g., the conductor) is the housing itself. For example, the compression surface may be the conductor element and receives a flow of electric current.

In another aspect, the heating system can include a heating element and a blower disposed within the support platform and/or compression paddle. The heating element heats a flow of fluid (e.g., air), which is then channeled across the non-patient contacting side of the compression surface and conducts heat through the housing towards the compressive surface. The blower and heating element are disposed outside of the imaging area such that image artifacts are eliminated. Additionally, since the flow of air is contained on the opposite side of the compression surface(s) no openings are required on the patient contacting surfaces. In yet another aspect, the heating system can include a heating element and a blower disposed within the support arm of the support platform and the compression paddle. The heating element heats a flow of air, and then, a baffle of directs the heated air across the compression surface of the support platform. By directly heating the compression surface, the efficiency of the heating system is increased. Furthermore, the outlet of the baffle is oriented in a downward direction and partially raised from the compression surface. Accordingly, infiltration of bodily fluids that accumulate on the compression surface is reduced or eliminated.

The heating systems described herein are shaped and sized to fit within the support platform and/or compression paddle such that patient contact therewith is eliminated. As such, there are no additional components to clean and sterilize after use. In some aspects, the heating system may include a temperature sensor that measures the temperature of the compression surface. The temperature sensor enables the operation of the heating system to be based at least partially on real time temperature measurements, thereby further increasing patient comfort. The temperature sensor is also disposed outside of the imaging area such that image artifacts are reduced and/or eliminated.

Figure 1B:
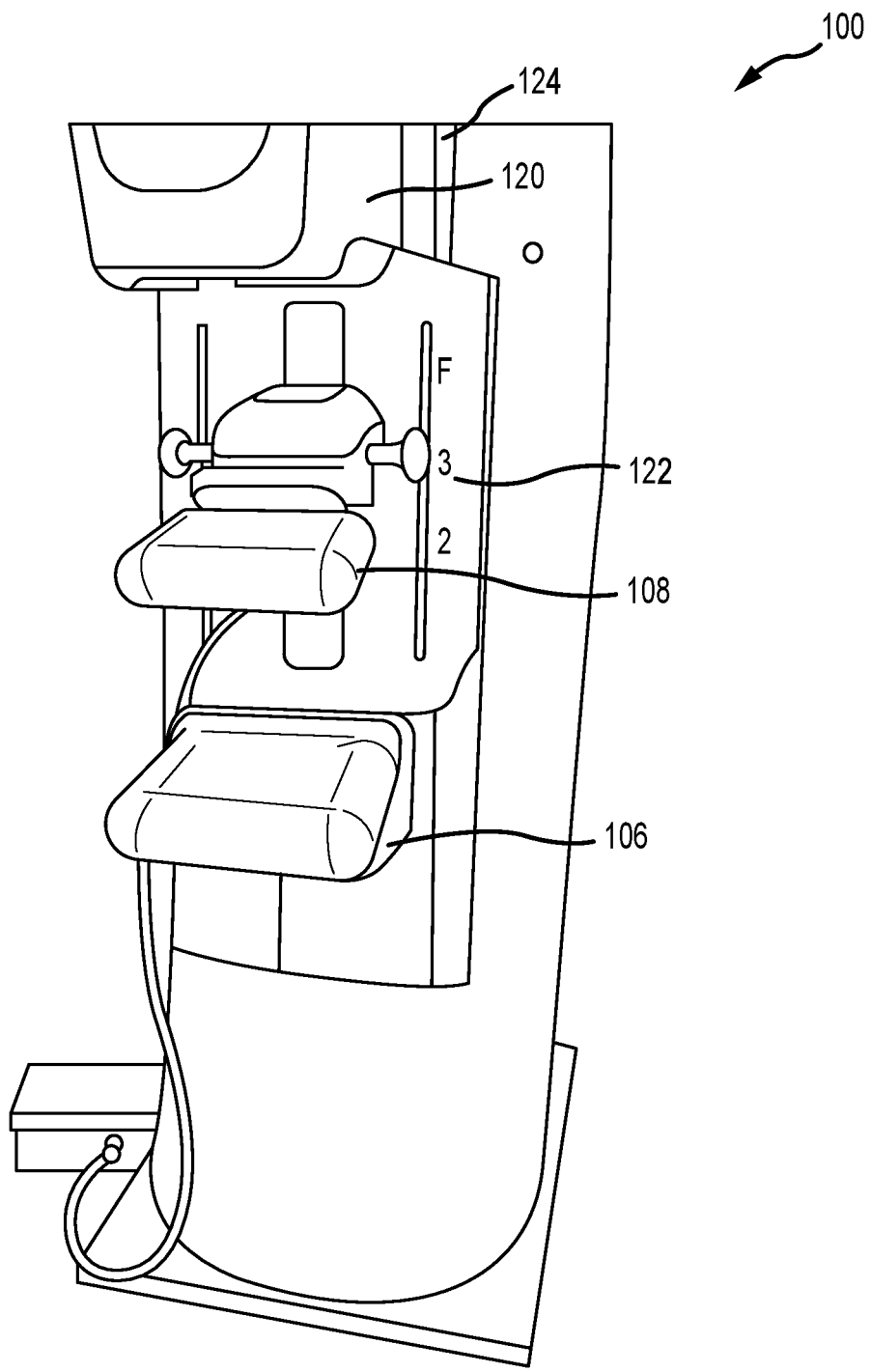
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 is configured to immobilize a patient's breast 102 for x-ray imaging (one or more of a mammography mode, a tomosynthesis mode, and a computed tomography (CT) mode) via a breast compression immobilizer unit or compression system 104. In the example, the compression system 104 includes a breast support platform 106 and a moveable compression paddle 108. The breast support platform 106 and the compression paddle 108 each have a compression surface 110 and 112, respectively, with the compression surface 112 configured to move towards the support platform 106 to compress and immobilize the breast 102. In known systems, the compression surfaces 110, 112 are exposed so as to directly contact the breast 102. The support platform 106 also houses an image receptor 114 and, optionally, a tilting mechanism 116. In some examples, the support platform 106 also houses an anti-scatter grid 117. The compression system 104 is in a path of an imaging x-ray beam 118 emanating from an x-ray source 120, such that the beam 118 impinges on the image receptor 114.

The compression system 104 is supported on a first support arm 122 and the x-ray source 120 is supported on a second support arm, also referred to as a tube arm 124. For mammography, support arms 122 and 124 can rotate as a unit about an axis 126 between different imaging orientations such as cranial-caudal (CC) and mediolateral oblique (MLO) views, so that the imaging system 100 can take a mammogram projection image at each orientation. In operation, the image receptor 114 remains in place relative to the support platform 106 while an image is taken. The immobilizer unit 104 releases the breast 102 for movement of support arms 122, 124 to a different imaging orientation. For tomosynthesis, the support arm 122 stays in place, with the breast 102 immobilized and remaining in place, while at least the tube arm 124 rotates the x-ray source 120 relative to the immobilizer unit 104 and the compressed breast 102 about the axis 126. The imaging system 100 takes plural tomosynthesis projection images of the breast 102 at respective angles of the x-ray beam 118 relative to the breast 102. As such, the compression system 104 and tube arm 124 may be rotated discrete from each other, unless matched rotation is required or desired for an imaging procedure.

In some examples, the anti-scatter grid 117 is positioned between the compression surface 110 and the image receptor 114 and is configured to reduce x-rays scattered by the breast tissue from reaching the image receptor 114 during mammography and/or tomosynthesis x-ray imaging. The anti-scatter grid 117 may include a plurality of septa formed from a radio-opaque material or a highly x-ray absorbing material, such as lead, and separated by interspaces that are formed from a radiolucent material or a low-x-ray attenuating material, such as carbon fiber or aluminum. In operation, the anti-scatter grid 117 moves relative to the image receptor 114 to reduce Moire patterns in the resulting images. The anti-scatter grid 117 may also retract away from the image receptor 114 as required or desired.

Concurrently and optionally, the image receptor 114 may be tilted relative to the breast support platform 106 and coordinated with the rotation of the second support arm 124. The tilting can be through the same angle as the rotation of the x-ray source 120, but may also be through a different angle selected such that the x-ray beam 118 remains substantially in the same position on the image receptor 114 for each of the plural images. The tilting can be about an axis 128, which can but need not be in the image plane of the image receptor 114. The tilting mechanism 116 that is coupled to the image receptor 114 can drive the image receptor 114 in a tilting motion. In some examples, the anti-scatter grid 117 may be coupled to the image receptor 114 such that the grid 117 tilts with the receptor 114. In other examples, the anti-scatter grid 117 may not tilt with the image receptor 114 and be independent therefrom.

For tomosynthesis imaging and/or CT imaging, the breast support platform 106 can be horizontal or can be at an angle to the horizontal, e.g., at an orientation similar to that for conventional MLO imaging in mammography. The imaging system 100 can be solely a mammography system, solely a CT system, or solely a tomosynthesis system, or a "combo" system that can perform multiple forms of imaging.

When the system is operated, the image receptor 114 produces imaging information in response to illumination by the imaging x-ray beam 118, and supplies it to an image processor 130 for processing and generating breast x-ray images. A system control and work station unit 132 including software controls the operation of the system and interacts with the operator to receive commands and deliver information including processed-ray images.

One challenge with the imaging system 100 is how to efficiently immobilize and compress the breast 102 for the desired or required imaging. A health professional, typically an x-ray technologist, generally positions and adjusts the breast 102 between the support platform 106 and the compression paddle 108 while pulling tissue towards the imaging area to immobilize the breast 102 and keep it in place, with as much of the breast tissue as practicable being between the compression surfaces 110, 112. However, when the support platform 106 and/or the compression paddle 108 are cold, the patient may experience discomfort and anxiety, which may result in movement and an improperly positioned breast. This even sometimes requires an x-ray image to be re-taken, which delivers unnecessary x-ray doses to the patient.

The imaging system 100 is typically disposed within a patient room that is relatively cold so as to facilitate imaging system operation. As such, the outer surfaces of the imaging system 100, for example, the compression surfaces 110, 112 are generally cold to the touch. Accordingly, a heating system 134 can be coupled to the support platform 106, the compression paddle 108, or both the support platform 106 and the compression paddle 108 to generate heat and increase the temperature of the compression surfaces 110, 112. For example, the typical temperature of the outer surfaces of an unheated imaging system 100 may be approximately 65° F. (about 18.3° C.) to 70° F. (about 21.1° C.), while the heating systems 134 may be configured to raise that temperature to approximately 85° F. (about 29.4° C.) to 90° F. (about 32.2° C.) or higher, thereby reducing patient discomfort and anxiety during the breast compression and imaging processes. Exemplary heating systems 134 are described in further detail below.

Figure 2A:
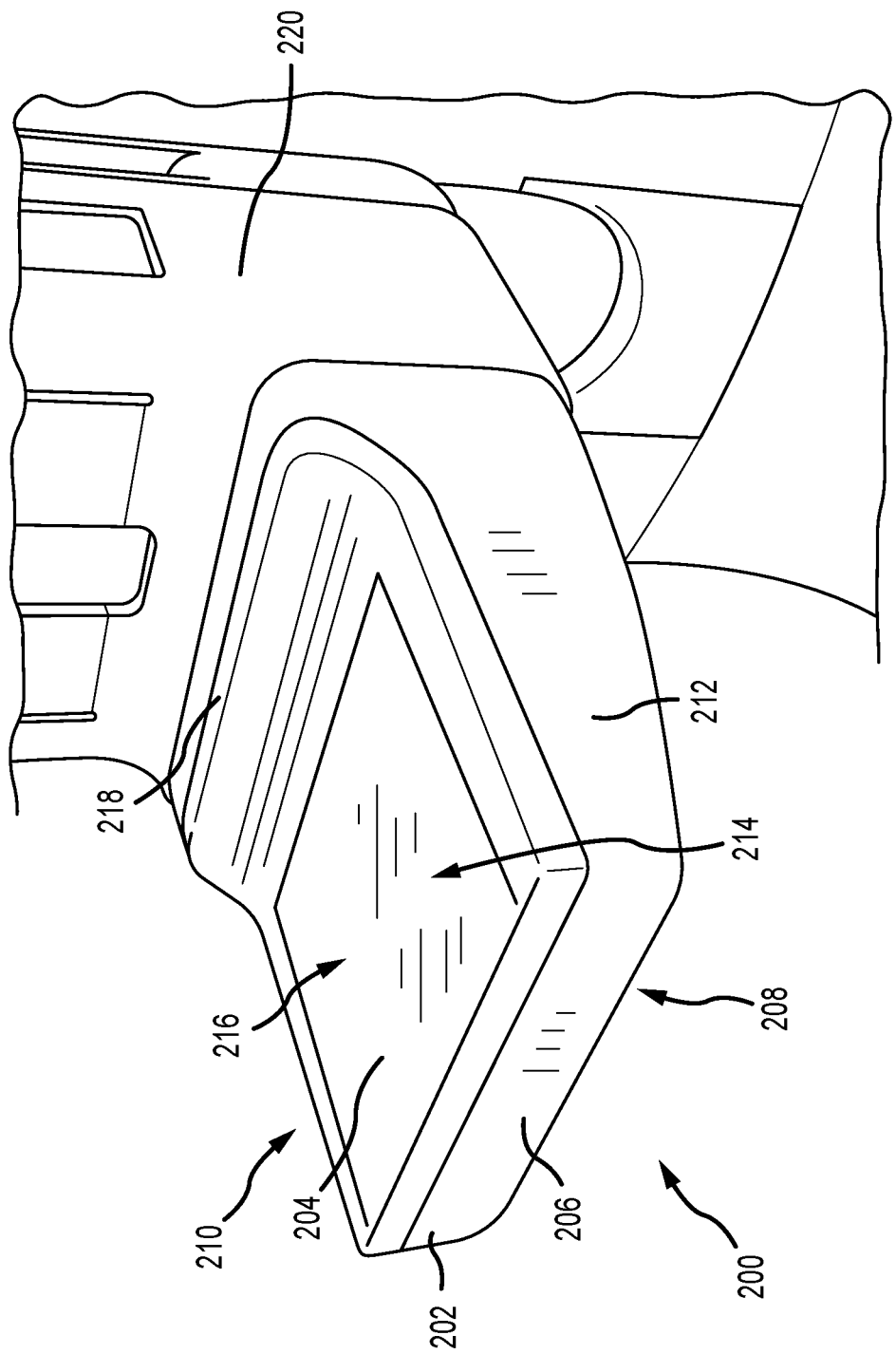
FIG. 2A is a perspective view of an exemplary breast support platform.

FIG. 2A is a perspective view of an exemplary breast support platform 200. The breast support platform 200 includes a housing 202 that houses the receptor and the anti-scatter grid (both not shown for clarity). The housing 202 includes a compression plate 204, a front wall 206, a bottom plate 208, and two sidewalls 210, 212 extending substantially orthogonal to the walls 204, 206, and 208. A compression surface 214 is formed on the outside surface of the compression plate 204. In operation, a patient's breast is supported on the compression surface 214 for compression and immobilization and a patient's chest wall is positioned against the front wall 206. The compression plate 204 is typically formed from a carbon fiber-based material, while the rest of the housing 202 is typically formed from a plastic-based material. In the example, at least a portion of the carbon fiber compression plate 204 may extend along the front wall 206 and/or sidewalls 210, 212.

An imaging area 216 is defined on the compression surface 214 that corresponds to the shape and size of the image receptor, and forms a visual perimeter boundary for breast placement on the compression surface 214. To enable imaging of breast tissue close to the patient's chest wall, the imaging area 216 extends from the front wall 206 towards a back portion 218 of the housing 202, which is coupled to a support arm 220. Generally, the imaging area 216 is positioned as close to the front wall 206 as possible so that as much breast tissue towards the chest wall of the patient can be imaged. The imaging area 216 is offset from both sidewalls 210, 212 to accommodate the tilting motion of the image receptor as described above.

In the example, the breast support platform 200 includes a heating system 222 (shown in FIG. 2B) disposed at least partially within the housing 202 and is configured to heat at least a portion of the compression plate 204 and/or at least a portion of the front wall 206. In some examples, at least a portion of the heating system 222 may be embedded within the housing 202. In other examples, the heating system 222 may be entirely enclosed within the housing 202. Additionally, at least a portion of the heating system 222 is mounted within the housing 202 outside of the imaging area 216, which allows the range of motion of the image receptor and the anti-scatter grid to be maintained.

Figure 2B:
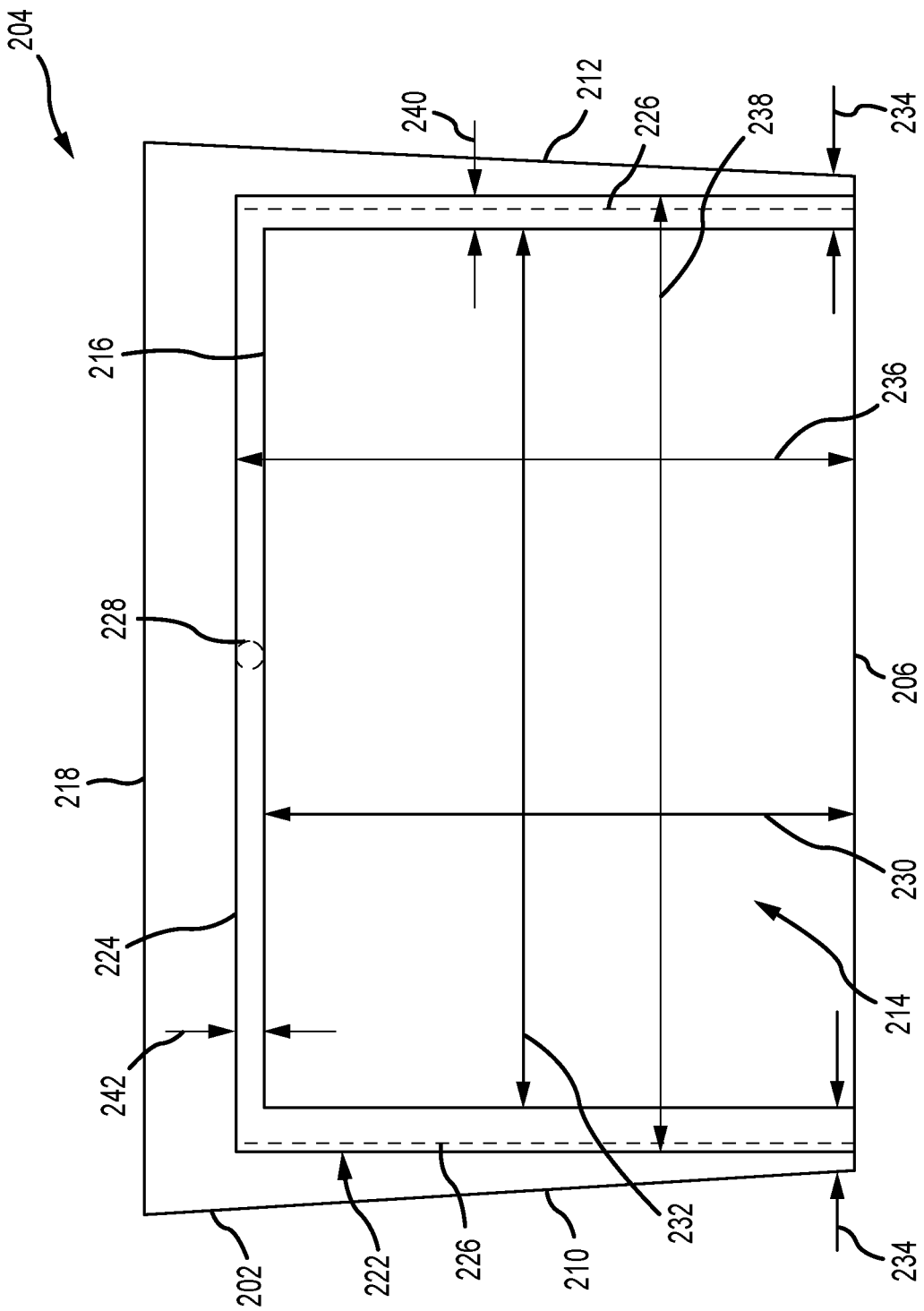
FIG. 2B is a top view of a compression surface of the breast support platform shown in FIG. 2A.

FIG. 2B is a top view of the compression plate 204 of the breast support platform 200 (shown in FIG. 2A). In FIG. 2B, the compression plate 204 is illustrated as transparent so that the position of the heating system 222 below the wall 204 may be shown. In the example, the heating system 222 includes a transparent conducting film 224 coupled to an inner surface of the compression plate 204 opposite of the compression surface 214. That is, the inner surface of the compression plate 204 is the non-patient contacting side of the support platform. The heating system 222 also includes electrical contact points 226 disposed on the transparent conducting film 224 and one or more temperature sensors 228. The transparent conducting film 224 is shaped and sized to completely cover the imaging area 216 so that the entire imaging area 216 may be heated for patient comfort. Furthermore, the contact points 226 and the temperature sensor 228 are disposed outside of the imaging area 216 so that image artifacts are reduced or eliminated.

In the example, the imaging area 216 is substantially rectangular and has a depth 230 extending from the front wall 206 towards the back portion 218, with a width 232 extending between the sidewalls 210, 212. In an aspect, the depth 230 may be approximately 240 millimeters (mm) and the width 232 may be approximately 290 mm. These dimensions form a clearance distance 234 of approximately 25 mm between the sidewalls 210, 212 of the housing 202 and the imaging area 216. This clearance distance 234 at least partially defines the space that the contact points 226 of the heating system 222 must fit within to eliminate undesirable image artifacts, while also enabling the movement of the image receptor and the anti-scatter grid. The transparent conducting film 224 is generally larger than the size of the imaging area 216 so that the contact points 226 and the temperature sensor 228 can be positioned outside of the imaging area 216. In the example, the transparent conducting film 224 is also substantially rectangular and has a depth 236 extending from the front wall 206 towards the back portion 218, with a width 238 extending between the sidewalls 210, 212. In an aspect, the depth 236 may be approximately 245 mm and the width 238 may be approximately 320 mm. These dimensions form a width overlap 240 proximate both sidewalls 210, 212 of approximately 15 mm for the contact points 226 and a depth overlap 242 proximate the back portion 218 of approximately 5 mm for the temperature sensor 228. It should be appreciated that these shapes and/or dimensions are exemplary only, and the imaging area 216 and transparent conducting film 224 may have any other size and/or shape that enables the heating system 222 to function as described herein.

By positioning the contact points 226 proximate the sidewalls 210, 212 and the temperature sensors 228 proximate the back portion 218, not only are image artifacts not formed, but also the image receptor and/or the anti-scatter grid are still able to move as described herein. For example, the image receptor and the anti-scatter grid may tilt up-to 30° and the illustrated placement of the heating system 222 still accommodates this movement. In other examples, the contact points 226 and/or the temperature sensors 228 may extend into the clearance space of the image receptor and/or the anti-scatter grid within the housing 202. For example, during imaging operations the image receptor and the anti-scatter grid typically move less than the maximum designed range of motion, and only tilt about 15°. As such, hard stops (not shown) for the image receptor and/or the anti-scatter grid may be positioned within the housing 202 to eliminate the components from contacting the heating system 222 when tilting more than 15°. In other examples, the placement of the contact points 226 and/or temperature sensors 228 may be at any other location that enables the heating system 222 to function as described herein.

As illustrated in FIG. 2B, the transparent conducting film 224 is positioned on the compression plate 204 and adjacent to the front wall 206 with the contact points 226 and the temperature sensors 228 disposed away from the front wall 206 so as to reduce image artifacts. Additionally or alternatively, the transparent conducting film 224 may extend at least partially along the front wall 206 of the housing 202. This enables the front wall 206 to be heated for patient comfort. However, because the image receptor and/or the anti-scatter grid are typically in a close clearance fit with the front wall 206, the front wall 206 can include a recess or pocket (not shown) so that the transparent conducting film 224 can be recessed at least partially within the front wall 206. This placement of the heating system 222 restricts or eliminates contact with the image receptor and/or the anti-scatter grid. In some examples, the heating system 222 may heat the compression plate 204 and the front wall 206 together. In other examples, the heating system 222 may heat the compression plate 204 and the front wall 206 independently. For example, the compression plate 204 and the front wall 206 each have a separate transparent conducting film 224 with contact points 226 and temperature sensors 228 coupled thereto.

In the example, the transparent conducting film 224 is heated via resistive heating, whereby electric current is passed through the film 224 to produce heat. In other examples, the compression plate 204 itself and/or any other portion of the housing 202 may act as the resistive heating element. For example, the contact points 226 may be directly electrically coupled to the compression plate 204 so that electric current can be passed directly through the compression plate 204. The compression plate 204 then acts as a conductor element and heats directly through resistive heating. In an aspect, the compression plate 204 is formed from a carbon fiber-based material that acts as the conductor element. In another aspect, a conductor element is weaved within the carbon fiber-based material for resistive heating. In the exampled, the transparent conducting film 224 is not required and the conductor element of the heating system 222 is embedded directly within the housing 202 (e.g., the compression plate 204). In still other examples, components of the transparent conducting film 224 can be embedded at least partially within the compression plate 204 and/or any other portion of the housing and act as the resistive heating element.

Figure 3:
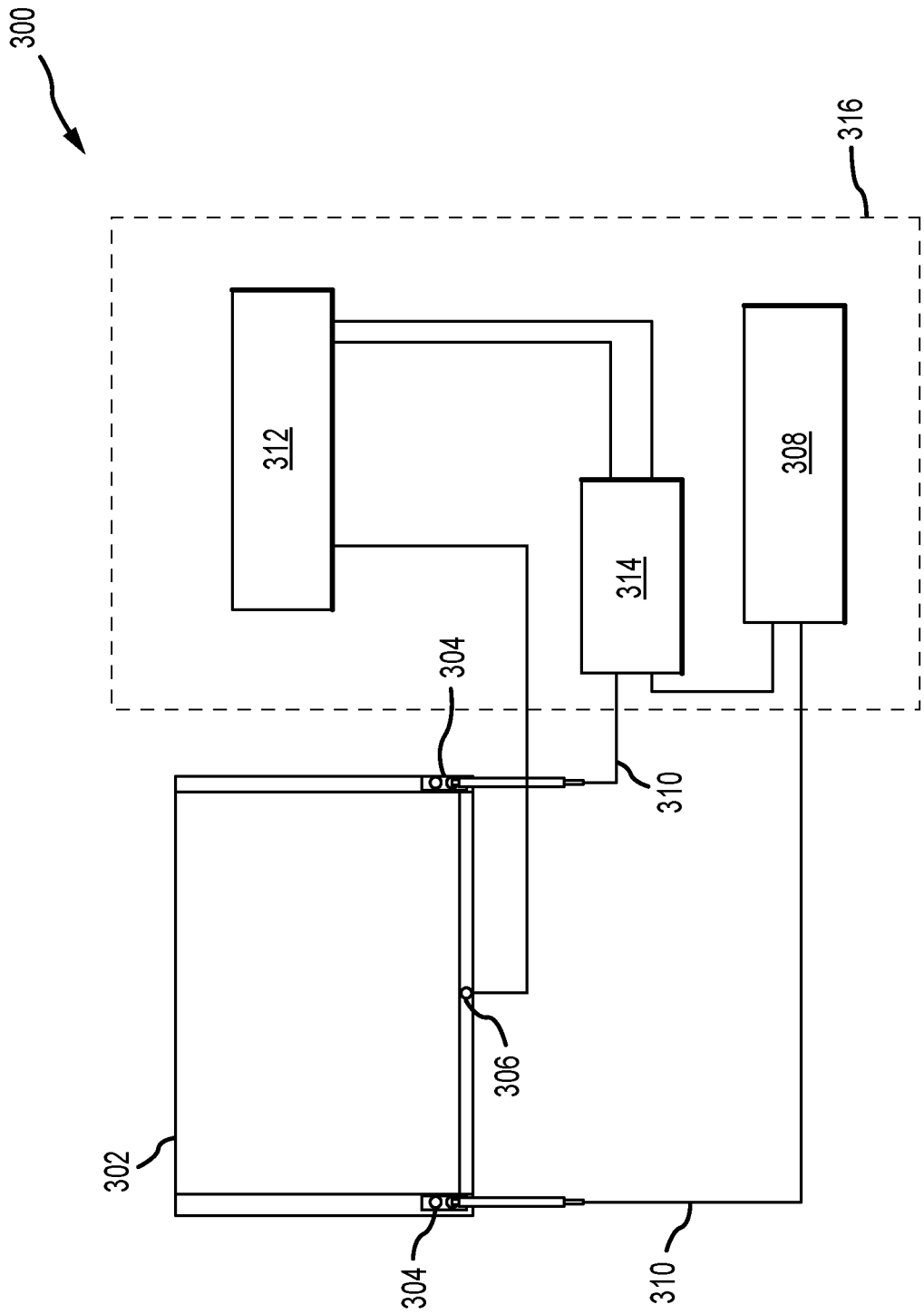
FIG. 3 is a schematic view of an exemplary heating system.

FIG. 3 is a schematic view of an exemplary heating system 300. As described above, the heating system 300 includes a transparent conducting film 302, electrical contact points 304, and a temperature sensor 306. The heating system 300 can be coupled to a breast support platform as described above in FIGS. 2A and 2B, and/or may be coupled to a compression paddle. The transparent conducting film 302 is coupled to a power source 308, via one or more wires 310 attached through the contact points 304 so that electrical current can flow thought the transparent conducting film 302, which generates heat. In aspects, the power source 308 is configured to produce between 1-5 amperes, between 1 and 150 volts, and about 50 watts. In one example, the power source 308 produces approximately 24 volts at approximately 50 watts.

The electric current that is channeled through the transparent conducting film 302 can be based on a measured temperature of the compression plate, as measured by the temperature sensor 306. The temperature sensor 306 is coupled to a controller 312 that is in communication with the power source 308 though a relay 314. As such, the electric current flowing through the transparent conducting film 302 can be controlled in real time so that the compression surface does not become too hot or too cold. In one example, the temperature sensor 306 may include one or more thermocouples. In other examples, temperature sensors 306 may be positioned on the image receptor, the anti-scatter grid, and/or the compression surface. Additionally, the power source 308, the controller 312, and/or the relay 314 may be disposed remote 316 from the support platform and/or compression paddle. For example, the remote components may be disposed in the support arm or the gantry of the imaging system.

In the example, the transparent conducting film 302 is configured to receive a flow of electric current and act as a resistor so as to generate heat. The generated heat then conducts through the compression plate. Generally, the carbon fiber compression plate conducts heat through the thickness of the plate better than conducting heat in a radially extending direction. As such, the transparent conducting film 302 is a planar sheet that covers the entire imaging area. In other examples, individual strips and/or patches of resistor film may be used as required or desired. In still other examples, heat tape, transparent conducting paint, or other conducting coatings may be used on the compression plate. In yet other examples, the compression plate may be formed from an electrically conductive material such that heat can be generated through the resistance of the plate material, although carbon fiber is only slightly electrically conductive. However, by adding the transparent conducting film 302 to the carbon fiber plate, the plate itself acts as an electric insulator so that electric current is not flowing through a component that is in direct contact with the patient.

The transparent conducting film 302 can be formed from indium tin oxide (e.g., ITO on glass or polycarbonate), transparent conductive oxides, conductive polymers, metal grids and random metallic networks, carbon nanotubs, graphene, nanowire meshes (e.g., silver nanowire or copper nanowire), ultra-thin metal films, etc. These materials are typically radiolucent such that the film 302 reduces or eliminates undesirable image artifacts in the x-ray image. The film 302 is configured to have a resistivity of up to 150 ohm/square. In one example, the resistivity is between 14 and 24 ohm/square. In another example, the resistivity can be between 1 and 20 ohm/square. In still another examples, the resistivity can be between 10 and 30 ohm/square. It should be appreciated that the above resistivity values are exemplary only, and the film 302 can have any resistivity value that enables the heating system 300 to function as described herein. As such, the plate can be the conductor that generates heat directly. However, as the resistivity of the film 302 increases, the electric current channeled through the film 302 is required to have higher voltages to produce heat. High voltages, however, are not necessary desirable for components in close patient proximity.

Figure 4:
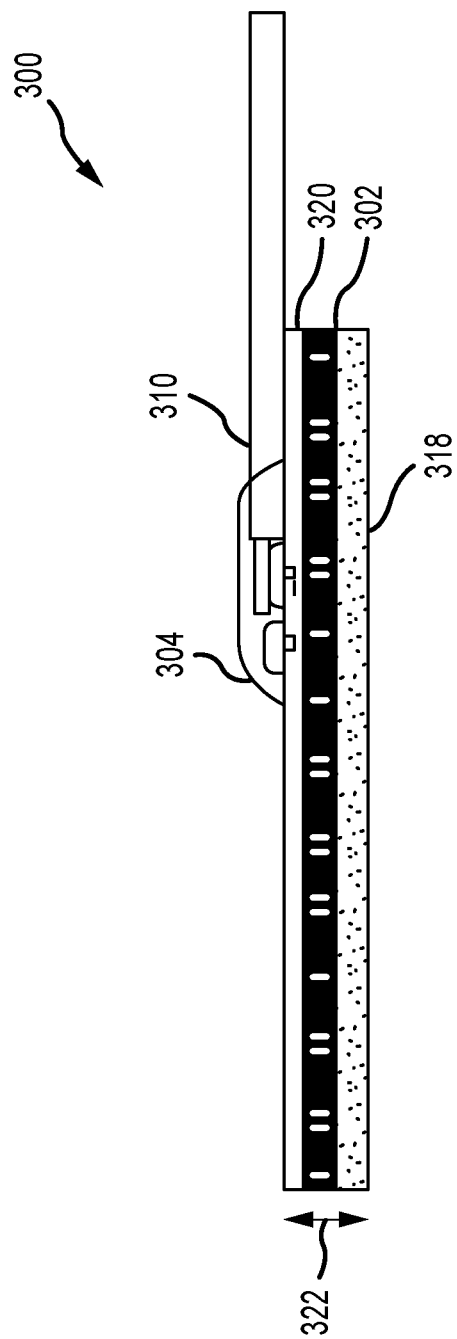
FIG. 4 is a cross section view of the heating system.

FIG. 4 is a cross section view of the heating system 300. The heating system 300 includes the transparent conducting film 302 that receives an electric current through the wire 310 that is coupled to the film 302 at the contact point 304. The transparent conducting film 302 is secured to the inner surfaces of the breast support platform by a transfer adhesive 318. The transfer adhesive 318 is resistant to dust and air bubbles so that undesirable image artifacts are reduced or eliminated from being formed during the x-ray imaging. In some examples, to reduce or eliminate dust and air bubbles in the adhesive 318, the heating system 300 can be secured to the breast support platform in a clean room and/or a static-free environment. This can form an adhesive 318 that is substantially devoid of dust and air bubbles therein. The transfer adhesive 318 is also heat resistant, but heat conductive, so that the transparent conducting film 302 remains adhered to the support platform and/or the compression paddle and is enabled to heat the compression surface.

In the example, a heat treated polyester layer 320 covers the one side of the transparent conducting film 302 opposite of the transfer adhesive 318. The polyester layer 320 insulates the breast support platform components (e.g., the image receptor and/or the anti-scatter grid) from the heat generated by the heating system 300. The contact point 304 (e.g., hot melt potting) is disposed on the polyester layer 320 side of the transparent conducting film 302. This positions the active side of the transparent conducting film 302 away from the support platform. In other examples, the transparent conducting film 302 has a thickness 322 that enables the contact point 304 to be at least partially encapsulated by the film 302.

Generally, the transparent conducting film 302 is relatively thin so that the film may be retrofit onto existing imaging systems and without modifying the profile of the support platform housing. For example, adjacent to the compression plate, there is generally enough space to attach the heating system 300 without having to move the image receptor and/or the anti-scatter grid. However, thicker transparent conducting films 302 (e.g., glass based films) may require the image receptor and/or the anti-scatter grid to be moved further away from the compression plate. Additionally, the thin low profile of the transparent conducing film 302 also reduces or eliminate interferences with the x-ray receptor. For example, heat and/or electromagnetic interferences with the receptor.

Figure 5:
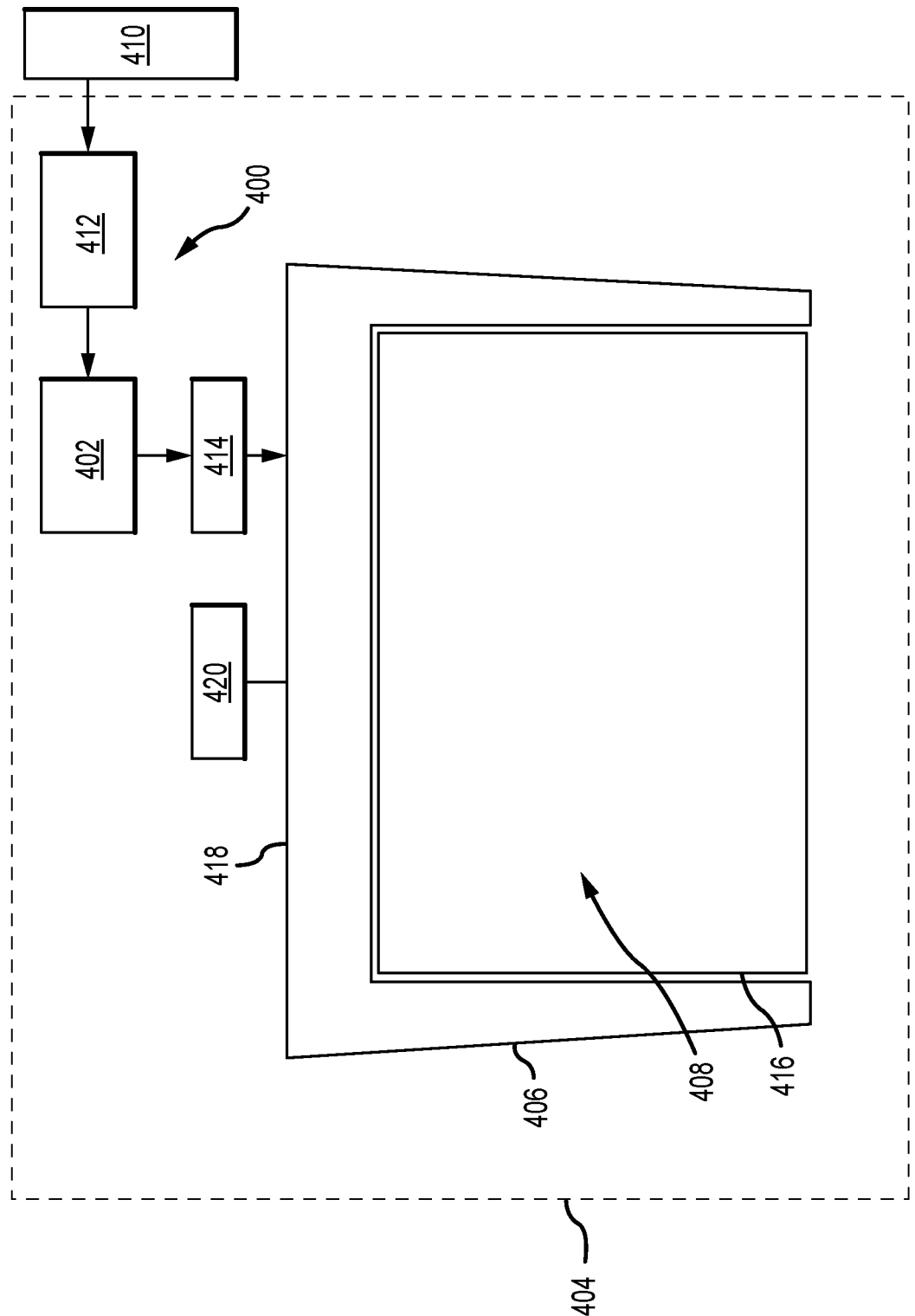
FIG. 5 is a schematic view of another heating system.

FIG. 5 is a schematic view of another heating system 400. In this example, the heating system 400 includes a blower 402 disposed at least partially within a housing 404 of the breast support platform and/or compression paddle. In some examples, the heating system 400 may be entirely enclosed within the housing 404. The blower 402 is oriented to channel hot air across an inner surface of a compression plate 406 so as to heat a compression surface 408 for patient comfort. The blower 402 is coupled in flow communication to a remotely positioned fluid source 410. In the example, the fluid source 410 channels a flow of fluid (e.g., air or other gaseous substance) to the blower 402 to expel across the inner surface of the compression plate 406. In other examples, a flow of liquid may be used as required or desired. A heating element 412 is positioned proximate the blower 402, either upstream or downstream, to heat the flow of fluid right before being expelled to the compression plate 406. Additionally, a baffle 414 or other flow directing device is positioned downstream of the blower 402 such that the flow of heated fluid can be directed within the housing 404 as required or desired. Generally, the heating system 400 is positioned so as to reduce fluid ingress into the housing 404 so as to reduce or eliminate heat interference with the x-ray receptor, while still enabling the heating of the compression surface 408 as described herein.

In the example, the blower 402 may direct the heated fluid flow directed towards the compression plate 406, or may generally heat the entire inside of the housing 404. Additionally, the heating system 400 is disposed outside of an imaging area 416 of the compression surface 408. This positions the heating system 400 away from the image detector and/or the anti-scatter device and does not form undesirable image artifacts during x-ray imaging. In one example, the heating system 400 may be positioned adjacent to a back portion 418 of the compression plate 406. In other examples, the heating system 400 may be located anywhere else within the housing 404 that enables the heating system 400 to function as described herein. Additionally, similar to the examples described above, the heating system 400 can include one or more temperature sensors 420 to measure the temperature of the compression surface 408 and to base operation of the heating system 400 therefrom (e.g., flow rate of blower 402 and temperature of heating element 412).

Figure 6:
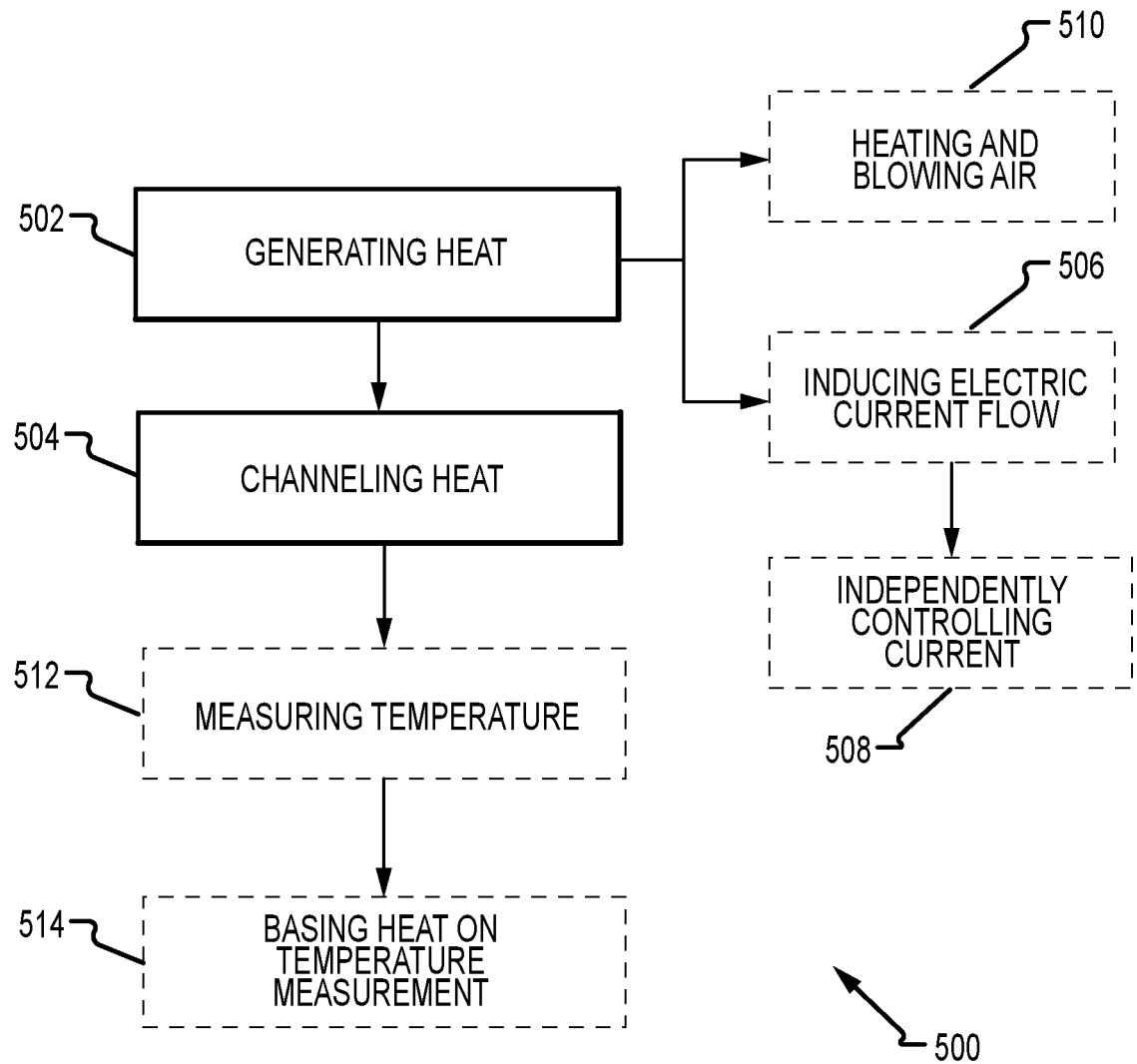
FIG. 6 depicts a flowchart illustrating a method of heating a breast support platform of an x-ray imaging system.

FIG. 6 depicts a flowchart illustrating a method 500 of heating a breast support platform of an x-ray imaging system. The method 500 includes generating heat through a heating system disposed at least partially within a housing of the breast support platform (operation 502). The housing includes at least a compression plate and a front wall. The method 500 further includes channeling the heat generated from the heating system towards at least a portion of the compression plate, at least a portion of the front wall, or at least a portion of the compression plate and the front wall (operation 504). The heat then conducts through the housing so that the breast support platform increases in temperature, thereby increasing patient comfort during breast compression and imaging procedures.

In some examples, generating heat (operation 502) may include inducing an electric current flow across a transparent conducting film coupled to an inner surface of the housing (operation 506). The resistance from the transparent conducting film generates the heat of the heating system. In other examples, the transparent conducting film is adjacent to at least a portion of the compression plate and the front wall. As such, the current applied to the transparent conducting film at the compression plate can be independently controlled from the current applied to the transparent conducting film at the front wall (operation 508). This enables the front wall to be heated to a different temperature from the compression plate as required or desired. In another aspect, generating heat (operation 502) may include inducing an electric current flow directly across the compression plate. The compression plate acting as the conductor element provides resistance and generates heat for the heating system. Alternatively, generating heat (operation 502) may include heating a flow of air and blowing the hot air across an inner surface of the housing (510). The method 500 may also include measuring a temperature of the support platform (operation 512) so that the heat generated by the heating system can be at least partially based on the temperature measured by the temperature sensor (operation 514).

Figure 7A:
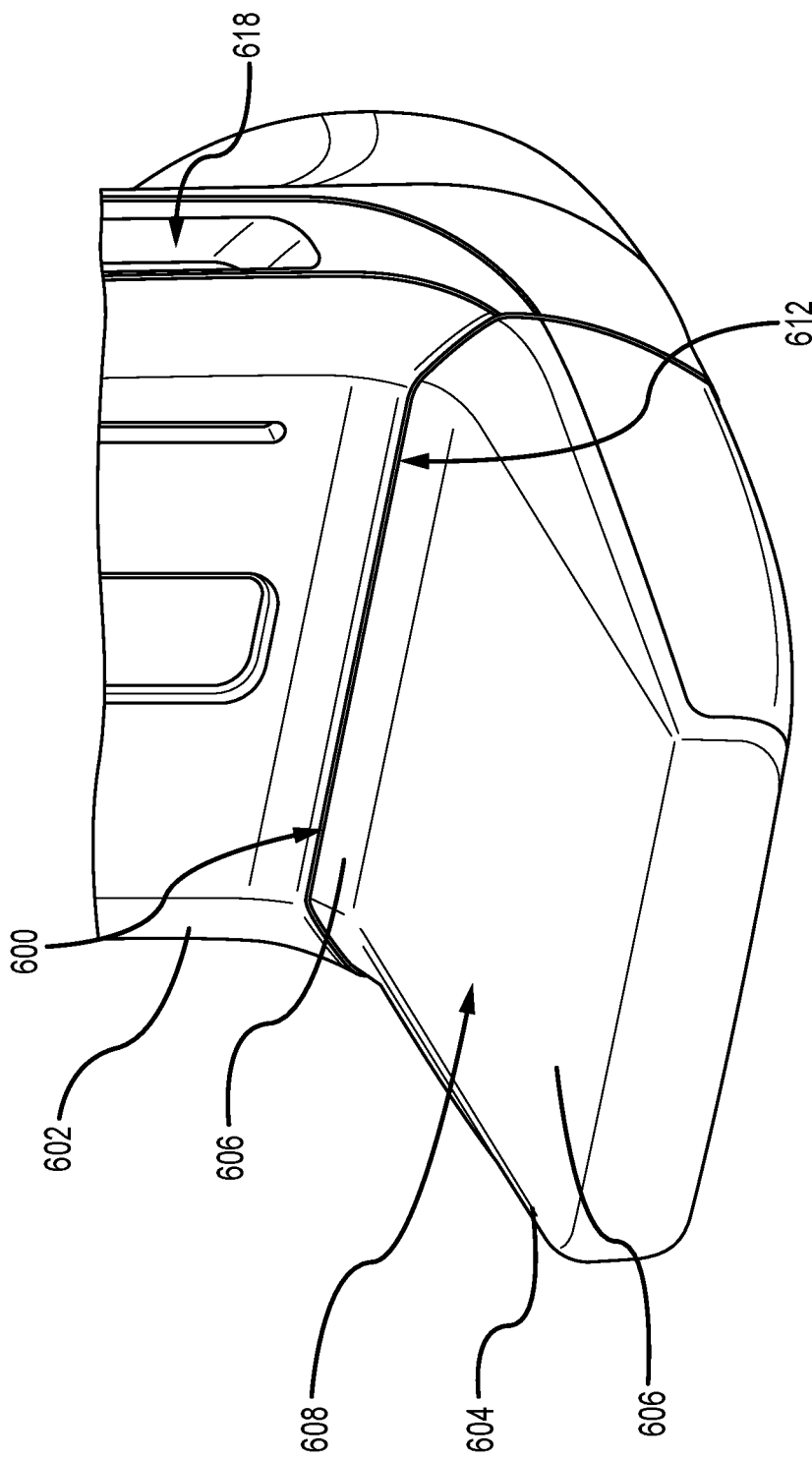
FIG. 7A is a perspective view of another heating system.
Figure 7B:
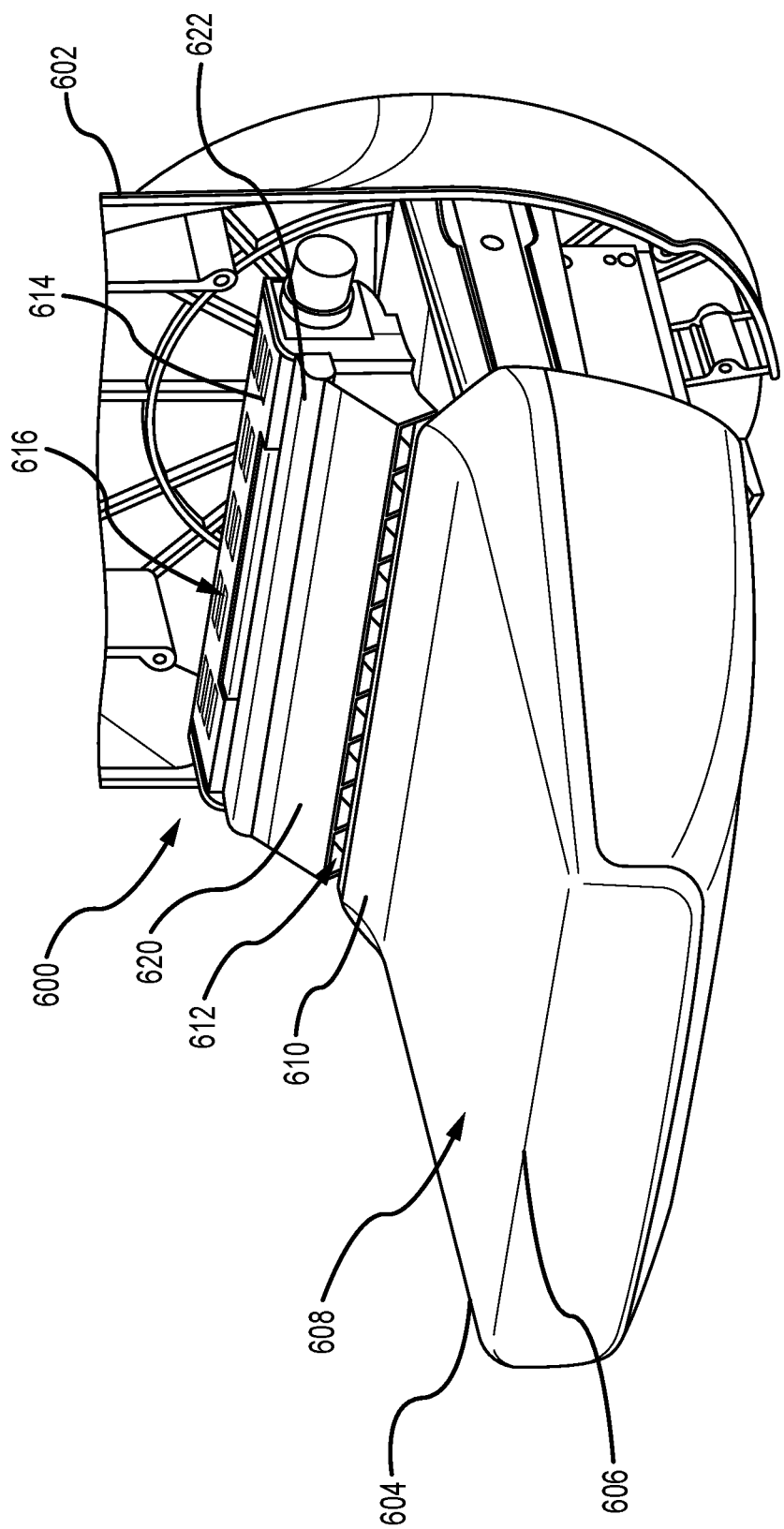
FIG. 7B is a perspective view of the heating system shown in FIG. 7A with a portion of a housing removed.
Figure 7C:
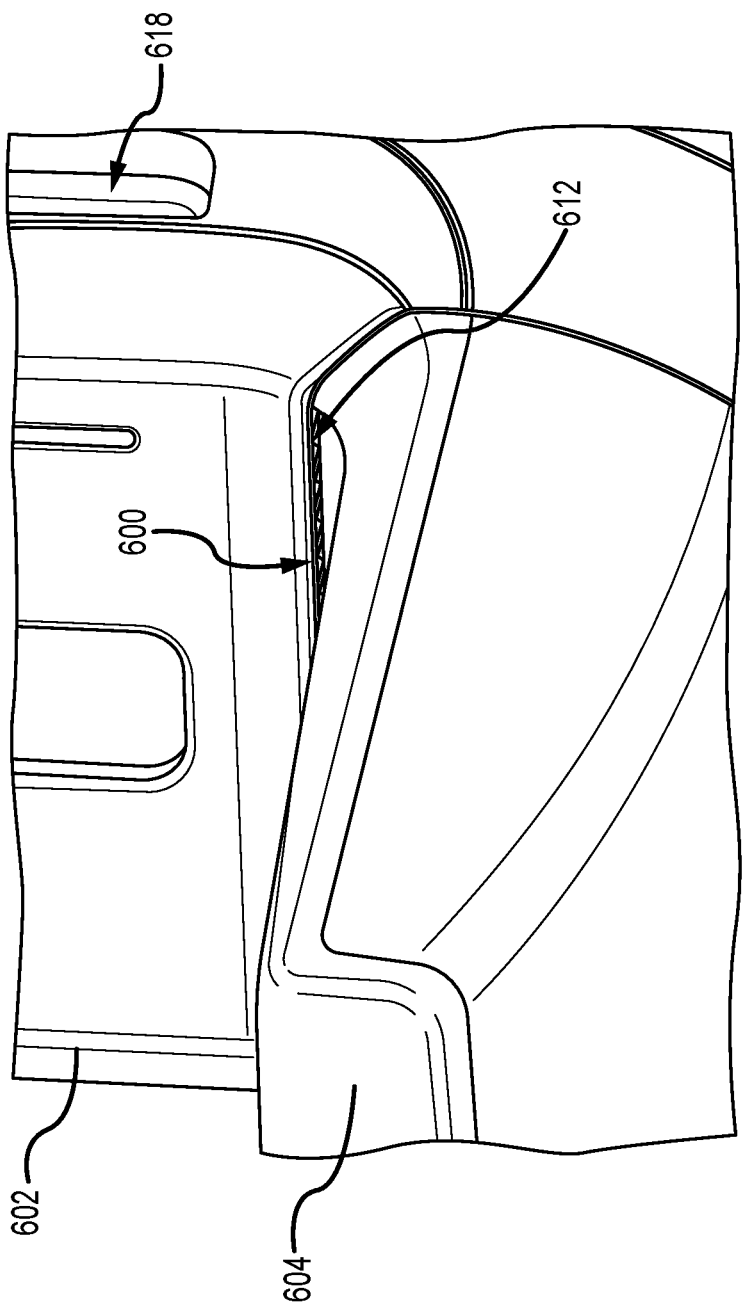
FIG. 7C is an enlarged perspective view of the heating system shown in FIG. 7A.

FIG. 7A is a perspective view of another heating system 600. FIG. 7B is a perspective view of the heating system 600 with a portion of a housing 602 removed. FIG. 7C is an enlarged perspective view of the heating system 600. In this example, the heating system 600 is at least partially disposed within a support arm housing 602 that supports a breast support platform 604 and a compression paddle (not shown). Similar to the examples described above, the breast support platform 604 houses a receptor (not shown) and has a compression plate 606 with a compression surface 608. The breast compression plate 606 includes a rear portion 610, which in this example, extends in an upwards direction from the compression surface 608. For example, the rear portion 610 may be substantially curved and positioned between the planar compression surface 608 and the housing 602. In this example, the heating system 600 includes an outlet 612 that is positioned adjacent to the rear portion 610 of the compression plate 606 so as to channel hot air towards the rear portion 610, which then directs the hot air across at least a portion of the compression surface 608. By channeling hot air across the compression surface 608, the compression surface 608 and/or a portion of the patient's breast may be heated for patient comfort before and/or during the compression procedure.

The heating system 600 includes a blower 614 that is positioned within the support arm housing 602 and at least partially above the breast support platform 604. In the example, the blower 614 may be a centrifugal fan (e.g., a squirrel cage fan) that is drum shaped with a plurality of blades that are mounted around a hub. The blower 614 can have one or more vents 616 such that air from within the housing 602 can be drawn through the blower 614. In some examples, the housing 602 may have one or more inlets 618 so that air can flow through the housing 602 and into the blower. Additionally, a baffle 620 extends between the blower 614 and the rear portion 610 of the compression plate 606. The baffle 620 forms the outlet 612 and may have one or more vanes that are configured to direct the flow across predetermined areas of the compression surface 608. A heating element 622 is positioned proximate the blower 614, either upstream or downstream, to heat the air before being expelled to the compression plate 606. Additionally, similar to the examples described above, the heating system 600 can include one or more temperature sensors (not shown) to measure the temperature of the compression surface 608 and to base operation of the heating system 600 therefrom (e.g., flow rate of blower 614 and temperature of heating element 622).

In the example, the heating system 600 is positioned so that the outlet 612, which provides the heating fluid, is above the compression plate 606 and facing in a substantially downward direction. As such, the heating system 600 is disposed outside of the imaging area such that image artifacts are eliminated and the operation of the receptor and anti-scatter grid (not shown) is not interfered with. Furthermore, the downward direction of the outlet 612 and the offset from the compression plate 606 reduce or eliminate infiltration of bodily fluids (e.g., sweat or blood—if biopsies are performed) that may accumulate on the compression surface 608. Additionally, by placing the outlet 612 in a close proximity to the compression surface 608, the efficiency and performance of the heating system 600 is increased.

Figure 8:
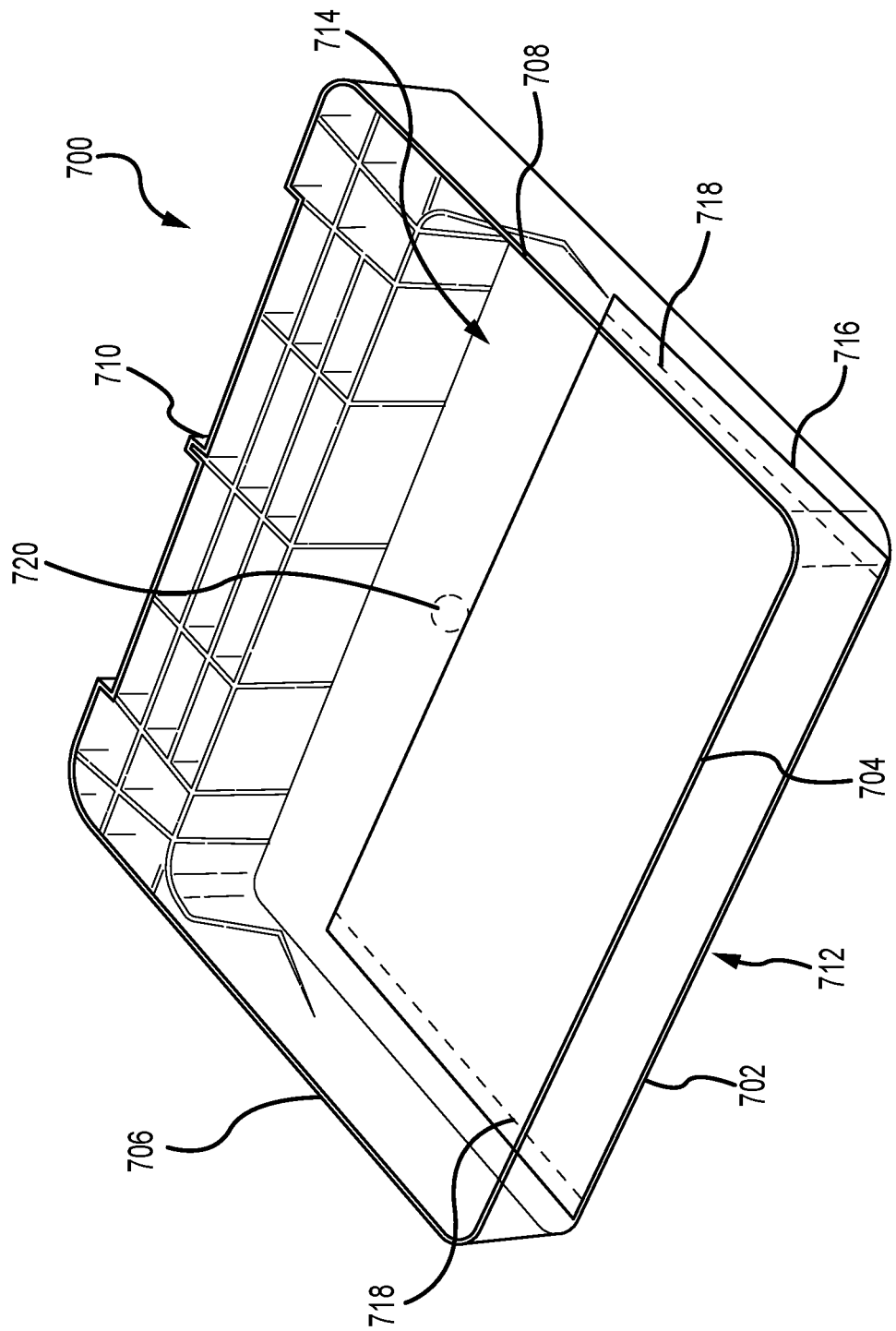
FIG. 8 is a perspective view of an exemplary compression paddle.

FIG. 8 is a perspective view of an exemplary compression paddle 700. The compression paddle 700 includes a compression plate 702, a front wall 704, two opposing sidewalls 706, 708, and a bracket 710. The compression plate 702 forms a bottom compression surface 712 for compressing the patient's breast against the support platform (e.g., the platform 200 and/or 604 described above). The front wall 704 of the paddle 700 is configured to be positioned against the patient's chest wall. The bracket 710 is sized and shaped to removeably couple to the support arm of the imaging system.

Additionally, the compression paddle 700 includes a heating system 714 configured to heat at least a portion of the compression plate 702 and/or at least a portion of the front wall 704. The heating system 714 can include a transparent conducting film 716 coupled to an outer surface of the compression plate 702 and opposite of the compression surface 712. That is, the outer surface of the compression plate 702 is the non-patient contacting side of the compression paddle 700 (e.g., a top surface). In some examples, the transparent conducting film 716 can be at least partially enclosed by the body of the compression paddle 700. In other examples, the compression plate 702 and/or any other portion of the paddle 700 may form the conductor element of the heating system 714 and directly receive a flow of electrical current as described herein. The heating system 714 also includes electrical contact points 718 disposed on the transparent conducting film 716 and one or more temperature sensors 720. The transparent conducting film 716 is shaped and sized to completely cover the imaging area so that the entire imaging area may be heated for patient comfort. In other examples, only a portion of the imaging area may be heated. Furthermore, the contact points 718 and the temperature sensor 720 are disposed outside of the imaging area so that image artifacts are reduced or eliminated.

As illustrated in FIG. 8, the transparent conducting film 716 is positioned on the compression plate 702 and adjacent to the front wall 704 with the contact points 718 and the temperature sensors 720 disposed proximate the sidewalls 706, 708 and/or the bracket 710 so as to reduce image artifacts. Additionally or alternatively, the transparent conducting film 716 may extend at least partially up the front wall 704 as required or desired. This enables the front wall 704 to be heated for patient comfort. In examples, the transparent conducting film 716 may be substantially similar to the film 302 described above in reference to FIGS. 3 and 4. In some examples, the compression surface 712 may be substantially curved as required or desired.

In other examples, the heating system 714 may include a blower (not shown) that can channel hot air across the compression plate 702 so as to heat at least a portion of the compression surface 712. Furthermore, because the heating system 714 is not positioned directly on the compression surface 712, during the compression procedure a height of the paddle 700 relative to the platform may still be used to directly measure breast thickness (e.g., for x-ray dose calculations).

As described herein, the exemplary heating systems are configured to heat at least a portion of a compression surface of a support platform and/or a compression paddle so as to reduce patient discomfort and anxiety during the breast compression and imaging process. This reduces undesirable movement of the patient and efficiency of the imaging process is increased. Generally, patients can feel discomfort during the breast compression process due to the compressive force applied to the breast. Additionally, the temperature (e.g., cold or low temperatures) of the compression surface(s) may also contribute to the patient's discomfort. In aspects of the present disclosure, the compression surface(s) can be heated so as to reduce patient discomfort. Additionally or alternatively, the heating systems can be used to distract the patient from the discomfort of the compression procedures. For example, selectively heating the compression surfaces to different temperatures and substantially maintaining the different temperatures during the compression process. This temperature change between the compression surfaces can induce a sensation (e.g., via the patient's thermoreceptors) on the patient's breast that acts to distract the patient during the compression process. Thereby, also reducing patient discomfort.

Using the heating systems described herein, the temperature change between the compression surface of the support platform and the compression surface of the compression paddle can be generated any number of ways. For example, the heating system may be coupled to the support platform so as to heat the compression surface, while the compression paddle remains at room temperature. In another example, the heating system may be coupled to the compression paddle so as to the heat the compression surface, while the support platform remains at room temperature. In still other examples, both the support platform and the compression paddle may have heating systems, but the compression surfaces of each are heated to different temperatures.

In some examples, room or unheated temperatures may be between approximately 65° F. (about 18.3° C.) to 70° F. (about 21.1° C.), while heated temperatures may be between approximately 85° F. (about 29.4° C.) to 90° F. (about 32.2° C.). In other examples, heated temperatures may raise to be between approximately 85° F. (about 29.4° C.) to 95° F. (about 35° C.). In still other examples, heated temperatures may raise to approximately 113° F. (about 45° C.). It should be appreciated that these temperature values are exemplary and the heated and unheated temperatures may be above or below the ranges as required or desired. As such, the temperature change between the support platform and the compression paddle can be between approximately 20° F. (about 11.1° C.) and 25° F. (about 13.9° C.) when one is unheated and the other is heated. When both the support platform and the compression paddle are heated, the temperature change can be between 10° F. (about 5° C.) and 30° F. (about 17° C.). In other examples, the temperature change between the heated support platform and the compression paddle can be less than or equal to 10° F. (about 5° C.) or greater than or equal to 30° F. (about 17° C.) as required or desired.

Figure 9:
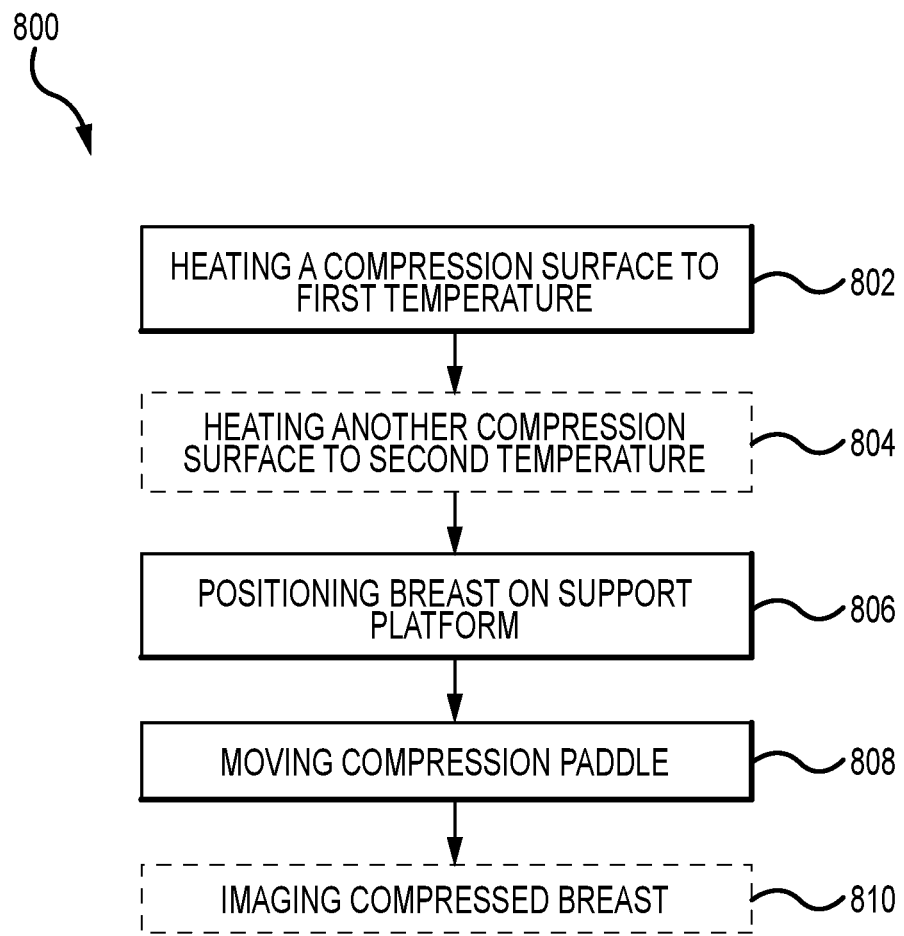
FIG. 9 depicts a flowchart illustrating a method of immobilizing a patient's breast on an x-ray imaging system.

FIG. 9 depicts a flowchart illustrating a method 800 of immobilizing a patient's breast on an x-ray imaging system. The method 800 includes heating at least a portion of a compression surface from one of a support platform and a compression paddle to a first temperature (operation 802). A compression surface of the other one of the support platform and the compression paddle is at a second temperature. In some examples, this other compression surface is heated to the second temperature (operation 804). As described above, each compression surface may have approximately equal heated temperatures (e.g., between approximately 85° F. (about 29.4° C.) to 95° F. (about 35° C.)). In other examples, each compression surface may have different temperatures. For example, one compression surface may be unheated, while the other compression surface may be heated. In another example, one compression surface may be heated, while the other compression surface is heated to a higher temperature. In an aspect, the temperature differences between the two compression surfaces may be at least 10° F. (about 5° C.). In some examples, the compression paddle may be heated on a separate paddle rack and then connected to the imaging system as required or desired, while the compression surface of the support platform can be held at constant heated temperature throughout the operational period of the imaging system.

Once one or more of the compression surfaces are heated (operation 802 and 804), the patient's breast can be positioned on the compression surface of the support platform by the technologist (operation 806). Then the compression paddle can be moved towards the support platform so as to compress the patient's breast between the two compression surfaces (operation 808). In some examples, the method 800 can then further include imaging the compressed breast in at least one of a mammography mode, a tomosynthesis mode, and a CT mode (operation 810).

By heating one or more of the compression surfaces, patient discomfort is reduced (e.g., by reducing cold surfaces). Additionally, by inducing a temperature differential between the two compression surfaces, a distraction sensation is generated to distract the patient from the compression procedure, thereby also reducing patient discomfort.

This disclosure describes some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art. Any number of the features of the different examples described herein may be combined into one single example and alternate examples having fewer than or more than all of the features herein described are possible. It is to be understood that terminology employed herein is used for the purpose of describing particular examples only and is not intended to be limiting. It must be noted that, as used in this specification, the singular forms "a," "an," and "the" include plural referents unless the context clearly dictates otherwise.

Although specific examples are described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of immobilizing a patient's breast on an x-ray imaging system, the method comprising:
heating at least a portion of one of a first compression surface of a support platform or a second compression surface of a paddle to a first temperature;
providing at least a portion of the other of the first compression surface of the support platform or the second compression surface of the paddle at a second temperature, the first temperature different than the second temperature, wherein providing at least a portion of the other of the first compression surface of the support platform or the second compression surface of the paddle at the second temperature comprises heating at least a portion of the other of the first compression surface of the support platform or the second compression surface of the paddle to the second temperature;

positioning the patient's breast on the first compression surface of the support platform; and moving the second compression surface of the compression paddle towards the support platform so as to immobilize the patient's breast between the first compression surface and the second compression surface.

2. The method of claim 1, wherein both the first temperature and the second temperature are between 29.4° C. and 35° C.

3. The method of claim 1, wherein the temperature difference is at least 5° C.

4. The method of claim 1, wherein the temperature difference is between 5° C. and 17° C.

5. The method of claim 1, further comprising imaging the immobilized breast in at least one of a mammography mode, a tomosynthesis mode, and a CT mode.

6. The method of claim 1, wherein heating the second compression surface of the paddle comprises heating the paddle on a paddle rack or heating via a transparent conducting film coupled to at least a portion of the paddle.

7. The method of claim 1, wherein heating the first compression surface of the support platform comprises heating via a transparent conducting film coupled to at least a portion of the support platform or a hot air blower.

8. The method of claim 1, further comprising measuring a temperature of the first compression surface.

9. The method of claim 8, further comprising measuring a temperature of the second compression surface.

10. The method of claim 1, wherein the first temperature and the second temperature are maintained during the immobilization of the patient's breast.

11. An immobilization system for an x-ray imaging system, the immobilization system comprising:
    a support arm;
    a breast support platform coupled to the support arm and including a first compression surface;
    a paddle coupled to the support arm and configured to move relative to the breast support platform, the paddle including a second compression surface; and
    a heating system configured to heat at least a portion of one of the first compression surface of the support platform or the second compression surface of the paddle to a first temperature, wherein at least a portion of the other of the first compression surface of the support platform or the second compression surface of the paddle is provided at a second temperature, the first temperature different than the second temperature, and wherein the heating system is configured to heat at least a portion of the other of the first compression surface of the support platform or the second compression surface of the paddle to the second temperature.

12. The immobilization system of claim 11, wherein the heating system comprises a first heating system for the first compression surface of the support platform and a separate second heating system for the second compression surface of the paddle.

13. The immobilization system of claim 11, wherein the heating system includes a transparent conductive film.

14. The immobilization system of claim 11, wherein the heating system includes a hot air blower.

15. The immobilization system of claim 11, further comprising a first temperature sensor configured to measure the first temperature of the first compression surface.

16. The immobilization system of claim 15, further comprising a second temperature sensor configured to measure the second temperature of the second compression surface.

17. The immobilization system of claim 11, wherein the second compression surface of the paddle is a curved surface.

18. The immobilization system of claim 11, wherein the immobilization system is coupled to an imaging system having an x-ray source and a detector disposed within the breast support platform, the imaging system operable in at least one of a mammography mode, a tomosynthesis mode, and a CT mode.

19. An immobilization system for an x-ray imaging system, the immobilization system comprising:
    a support arm;
    a breast support platform coupled to the support arm and including a first compression surface;
    a paddle coupled to the support arm and configured to move relative to the breast support platform, the paddle including a second compression surface;
    a heating system configured to heat at least a portion of one of the first compression surface of the support platform or the second compression surface of the paddle to a first temperature, wherein at least a portion of the other of the first compression surface of the support platform or the second compression surface of the paddle is provided at a second temperature, the first temperature different than the second temperature;
    a first temperature sensor configured to measure the first temperature of the first compression surface; and
    a second temperature sensor configured to measure the second temperature of the second compression surface.

* * * * *